United States Patent [19]

Partis et al.

[11] Patent Number: 4,761,503

[45] Date of Patent: Aug. 2, 1988

[54] PHARMACEUTICAL COMPOSITIONS CONTAINING 5-PHENYL-1,3-DIOXOALKENYL COMPOUNDS

[75] Inventors: Richard A. Partis, Evanston; Richard A. Mueller, Glencoe, both of Ill.

[73] Assignee: G. D. Searle & Co., Chicago, Ill.

[21] Appl. No.: 928,505

[22] Filed: Nov. 7, 1986

Related U.S. Application Data

[62] Division of Ser. No. 845,309, Mar. 28, 1986, Pat. No. 4,649,157.

[51] Int. Cl.$^4$ .............................................. C07C 45/46
[52] U.S. Cl. .................................. 568/313; 568/306; 564/169; 560/51; 560/53
[58] Field of Search ................ 568/313, 306; 564/169; 560/51, 53

[56] References Cited

U.S. PATENT DOCUMENTS

3,578,702  5/1971  Snapp et al. ..................... 568/313
3,759,929  9/1973  Klotmann ......................... 568/313
4,521,629  6/1985  Cortese et al. .................... 568/313

FOREIGN PATENT DOCUMENTS

1280849  10/1968  Fed. Rep. of Germany ...... 568/313
2501220   7/1976  Fed. Rep. of Germany ...... 568/313

OTHER PUBLICATIONS

Lehnert, Tetrahedrod, vol. 28, pp. 663–666 (1972).

Primary Examiner—James H. Reamer
Attorney, Agent, or Firm—Richard E. L. Henderson; Mary Jo Kanady; Paul D. Matukaitis

[57] ABSTRACT

This invention relates to pharmaceutical compositions containing a class of 5-phenyl-1,3-dioxoalkenyl compounds useful as inhibitors of leukotriene biosynthesis and thus useful in the treatment of conditions associated with leukotrienes. This invention also relates to the use of the 5-phenyl-1,3-dioxoalkenyl compounds in the inhibition of leukotriene biosynthesis and thus in the treatment of conditions associated with leukotrienes. This invention further relates to a novel process for the preparation of the 5-phenyl-1,3-dioxoalkenyl compounds.

16 Claims, No Drawings

PHARMACEUTICAL COMPOSITIONS CONTAINING 5-PHENYL-1,3-DIOXOALKENYL COMPOUNDS

This is a division of application Ser. No. 845,309 filed Mar 28, 1986 now U.S. Pat. No. 4,649,157.

BACKGROUND OF THE INVENTION (a) Field of the Invention

This invention relates to pharmaceutical compositions containing a class of 5-phenyl-1,3-dioxoalkenyl compounds useful as inhibitors of leukotriene biosynthesis. This invention also relates to the use of 5-phenyl-1,3-dioxoalkenyl compounds as inhibitors of leukotriene biosynthesis. By inhibiting leukotriene biosynthesis, the 5-phenyl-1,3-dioxoalkenyl compounds of this invention are useful in preventing or alleviating conditions associated with leukotrienes, such as allergic reactions, inflammatory conditions, certain skin disorders, hyperalgetic conditions, and coronary vasoconstriction.

Arachidonic acid is converted enzymatically to various biologically active products, such as prostaglandins, thromboxanes, various hydroxyeicosatetraenoic and hydroperoxyeicosatetraenoic acids, and leukotrienes. The leukotrienes, products of the 5-lipoxygenase pathway, are implicated in allergic reactions, particularly asthma, see M. Griffin et al., *N. Engl. J. Med.*, 308, 436–439 (1983); inflammatory conditions; skin diseases such as psoriasis; hyperalgetic conditions, see J. D. Levine et al., *J. Neuroscience*, 5, 3025–3029 (1985); and coronary vasoconstriction. One leukotriene, $LTD_4$, is the major active constituent of slow reacting substance of anaphylaxis (SRS-A), a potent bronchoconstrictor that is released during allergic reactions. See R. A. Lewis and K. F. Austen, *Nature*, 293, 103–108 (1981). When administered to humans and guinea pigs, $LTD_4$ causes bronchoconstriction by two mechanisms: (1) directly by stimulating smooth muscle; and (2) indirectly through release of thromboxane $A_2$, which causes contraction of respiratory smooth muscle. Because antihistamines are ineffective in the management of asthma, SRS-A is believed to be a mediator of the bronchoconstriction occurring during an allergic attack. $LTD_4$ may also be involved in other inflammatory conditions such as rheumatoid arthritis. Furthermore, $LTD_4$ is a potent coronary vasoconstrictor and influences contractile force in the myocardium and coronary flow rate of the isolated heart. See F. Michelassi et al., *Science*, 217, 841–843 (1982); J. A. Burke et al., *J. Pharmacol. and Exp. Therap.*, 221, 235–241 (1982). Another leukotriene, $LTC_4$, is also a very potent bronchoconstrictor. A third leukotriene, $LTB_4$, is associated with leukocyte chemotaxis, a phenomenon in which leukocytes migrate from the blood to an inflammatory site in response to chemical or biological stimuli, and may be involved in both acute and chronic inflammation. $LTB_4$ also appears to be associated with rheumatoid spondylitis and gout. Thus, the 5-lipoxygenase inhibitors of this invention, by inhibiting the production of leukotrienes, may prevent or alleviate the allergic, inflammatory, and vasoconstrictive conditions associated with leukotrienes.

Non-steroidal antiinflammatory agents, such as aspirin, indomethacin, ibuprofen, and the like, inhibit prostaglandin biosynthesis by blocking the cyclooxygenase pathway of arachidonic acid metabolism. As a consequence, leukotriene levels may increase as arachidonic acid is metabolized along the 5-lipoxygenase pathway, producing allergic reactions. Administration of 5-lipoxygenase inhibitors of this invention may be effective in reducing undesirable side effects associated with non-steroidal antiinflammatory agents when administered separately or in combination.

See (1) P. Sirois, "Pharmacology of Leukotrienes" in *Advances in Lipid Research*, 21, 79–101 (1985); (2) M. K. Bach, "Inhibitors of Leukotriene Synthesis and Action" in *The Leukotrienes: Chemistry and Biology*, L. W. Chakrin and D. M. Bailey, eds., pp. 163–194 (Orlando: Academic Press, 1984); (3) M. K. Bach, *Bioch. Pharmacol.*, 33, 515–521 (1984); (4) C. W. Lee et al., "Human Biology and Immunoreactivity of Leukotrienes" in *Advances in Inflammation Research*, 6, 219–225 (1984); (5) P. Sharon and W. F. Stenson, *Gastroenterology*, 84, 454–460 (1984); (6) E. L. Becker, *Trends Pharmacol Sci.*, 4, 223–225 (1983); (7) Editorial, "Leukotrienes and Other Lipoxygenase Products in the Pathenogenesis and Therapy of Psoriasis and Dermatoses" in *Arch. Dermatol.*, 119, 541–547 (1983); (8) B. Samuelsson, *Science*, 220, 568–575 (1983); (9) R. A. Lewis et al, *Int. J. Immunopharmac.*, 4, 85–90 (1982); (10) M. W. Musch et al., *Science*, 217, 1255–1256 (1982).

Unlike earlier therapeutic agents that treat symptoms rather than causes, the compounds of this invention and the pharmaceutical compositions thereof block the formation of causative mediators of allergic and inflammatory conditions and are therefore useful in the treatment of allergic reactions, inflammation, and other conditions associated with leukotrienes.

This invention also relates to a process that permits the unexpectedly efficient and convenient preparation of the 5-phenyl-1,3-dioxoalkenyl compounds of this invention. More specifically, this invention relates to a process for preparing 5-phenyl-1,3-dioxoalkenyl compounds in improved overall yield and purity by condensing optionally substituted benzaldehydes with acetoacetate esters, acetoacetamides, and 2,4-alkanediones.

(b) Prior Art

Condensation reactions of acetoacetate esters, acetoacetamides, or 2,4-alkanediones of the general formula $CH_3(C=O)CH_2(C=O)-R$ with benzaldehydes normally occur at the active methylene ($CH_2$) group rather than at the methyl group. See, e.g., J. March, *Advanced Organic Chemistry*, 2nd edition, pp. 854–859 (New-York: McGraw-Hill Book Company, 1977). Condensation at the methyl group has been reported to occur only under harsher conditions or by using more elaborate procedures than employed in the process of the present invention. For example, one method for preparing 5-phenyl-3-oxoalkenoates requires formation of a β-keto ester dianion (by addition of two separate strong bases), followed by addition of an aldehyde and dehydration of the initially formed alcohol. S. N. Hucklin and L. Weiler, *Tetrahedron Lett.*, 4835–4838 (1971). Another method for preparing 5-phenyl-3-oxoalkenoates requires forming an enol silyl ether from the corresponding β-keto ester dianion, followed by reaction with the aldehyde, generally in the presence of an activating reagent such as titanium tetrachloride. T.-H. Chan and P. Brownbridge, *J.C.S. Chem. Comm.* 578–579 (1979); T.-H. Chan and P. Brownbridge, *J.C.S. Chem. Comm.*, 20–21 (1981).

A condensation procedure employing titanium tetrachloride under conditions similar to those used in the present invention has been published, but the product compounds disclosed, unlike those of the present invention, are formed by a condensation reaction at the active methylene group and not by reaction at the methyl group. W. Lehnert, *Synthesis*, 667–669 (1974); W. Lehnert, *Tetrahedron*, 28, 663–666 (1972).

SUMMARY OF THE INVENTION

This invention relates to pharmaceutical compositions containing a class of 5-phenyl-1,3-dioxoalkenyl compounds of Formula I:

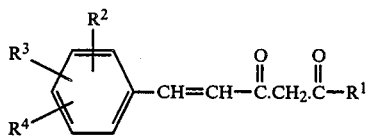

together with one or more non-toxic pharmaceutically acceptable carriers;
wherein $R^1$ is:
(a) hydrogen;
(b) $C_1$–$C_{10}$ alkyl;
(c) $C_1$–$C_6$ alkoxy;
(d) $NR^5R^6$;
wherein $R^5$ and $R^6$, each being the same or different, are:
(i) hydrogen; or
(ii) $C_1$–$C_{10}$ alkyl;
(e) phenyl or phenyl substituted with 1 to 3 substituents selected from the group consisting of:
(i) $C_1$–$C_{10}$ alkyl;
(ii) $C_1$–$C_6$ alkoxy;
(iii) nitro, with proviso that only one such substituent may be nitro; or
(iv) halogen;
(f) phenoxy or phenoxy substituted with 1 to 3 substituents selected from the group consisting of:
(i) $C_1$–$C_{10}$ alkyl;
(ii) $C_1$–$C_6$ alkoxy;
(iii) nitro, with the proviso that only one such substituent may be nitro; or
(iv) halogen;
(g)

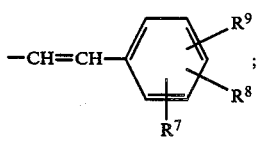

wherein $R^7$, $R^8$, and $R^9$, each being the same or different, are:
(i) hydrogen;
(ii) $C_1$–$C_{10}$ alkyl;
(iii) $C_1$–$C_6$ alkoxy;
(iv) benzyl;
(v) phenoxy or phenoxy substituted with 1 to 3 substituents selected from the group consisting of:
(A) $C_1$–$C_{10}$ alkyl;
(B) $C_1$–$C_6$ alkoxy; or
(C) halogen;
(vi) nitro, with the proviso that only one of $R^7$, $R^8$, and $R^9$ may be nitro;
(vii) halogen;
(viii) hydroxyl; or
(ix) $R^7$ and $R^8$ together are —CH=CH—CH=CH—;

wherein $R^2$, $R^3$, and $R^4$, each being the same or different, are:
(a) hydrogen;
(b) $C_1$–$C_{10}$ alkyl;
(c) $C_1$–$C_6$ alkoxy;
(d) benzyl;
(e) phenoxy or phenoxy substituted with 1 to 3 substituents selected from the group consisting of:
(i) $C_1$–$C_{10}$ alkyl;
(ii) $C_1$–$C_6$ alkoxy; or
(iii) halogen;
(f) nitro, with the proviso that only one of $R^2$, $R^3$, and $R^4$ may be nitro;
(g) halogen;
(h) hydroxyl; or
(i) $R^2$ and $R^3$ together are —CH=CH—CH=CH—.

The term "$C_1$–$C_{10}$ alkyl" refers to straight or branched chain alkyl groups having from 1 to 10 carbon atoms, also referred to as lower alkyl. Examples of $C_1$–$C_{10}$ alkyl are methyl, ethyl, propyl, butyl, pentyl, hexyl, heptyl, octyl, nonyl, decyl, and the isomeric forms thereof.

The term "$C_1$–$C_6$ alkoxy" refers to straight or branched chain alkoxy groups having from 1 to 6 carbon atoms. Examples of $C_1$–$C_6$ alkoxy are methoxy, ethoxy, propoxy, butoxy, pentoxy, hexoxy, and the isomeric forms thereof.

Examples of halogen are fluorine, chlorine, bromine, and iodine.

Although the structure shown for Formula I indicates one tautomeric form, it is understood that this representation is for convenience only and that the scope of this invention includes as equivalents all tautomeric keto and enol forms of the compounds of this invention.

This invention also relates to the use of a class of 5-phenyl-1,3-dioxoalkenyl compounds of Formula I in the treatment of conditions associated with leukotrienes.

This invention further relates to a process for preparing the 5-phenyl-1,3-dioxoalkenyl compounds of Formula I more efficiently and conveniently than is possible by other known methods. More specifically, the process of this invention involves the preparation of compounds of Formula I by condensing optionally substituted benzaldehydes with acetoacetate esters, acetoacetamides, or 2,4-alkanediones in the presence of a transition metal Lewis acid, preferably titanium tetrachloride, and an organic amine.

DESCRIPTION OF THE INVENTION

The 5-phenyl-1,3-dioxoalkenyl compounds of this invention, Formula I, are prepared by condensing, in the presence of a transition metal Lewis acid and of an organic amine, optionally substituted benzaldehydes of Formula II

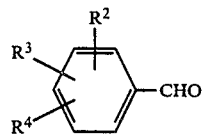

wherein $R^2$, $R^3$, and $R^4$ are above defined; with acetoacetate esters, acetoacetamides, or 2,4-alkanediones of Formula III

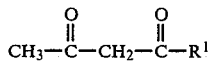

III wherein R[1] is:
(a) hydrogen;
(b) $C_1$–$C_{10}$ alkyl;
(c) $C_1$–$C_6$ alkoxy;
(d) $NR^5R^6$;
wherein $R^5$ and $R^6$, each being the same or different, are:
  (i) hydrogen; or
  (ii) $C_1$–$C_{10}$ alkyl;
(e) phenyl or phenyl substituted with 1 to 3 substituents selected from the group consisting of:
  (i) $C_1$–$C_{10}$ alkyl;
  (ii) $C_1$–$C_6$ alkoxy;
  (iii) nitro, with the proviso that only one such substituent may be nitro; or
  (iv) halogen;
(f) phenoxy or phenoxy substituted with 1 to 3 substituents selected from the group consisting of:
  (i) $C_1$–$C_{10}$ alkyl;
  (ii) $C_1$–$C_6$ alkoxy;
  (iii) nitro, with the proviso that only one such substituent may be nitro; or
  (iv) halogen.

Under the reaction conditions employed in the process of this invention, condensation occurs at the $CH_3CO$- methyl group of compounds of Formula III to form compounds of this invention rather than at the $-CO-CH_2-CO-$ methylene group of compounds of Formula III. The process of this invention possesses several advantages with respect to prior art methods. In particular, the process of this invention does not require generating or isolating special intermediate species such as those characterizing the prior art methods described above. For example, the present process does not require forming a discrete dianion intermediate, thus avoiding the need for strong base. Furthermore, the present process does not employ a silylated or other such intermediate, thus avoiding complexities necessitated by an initial silylation, a separate condensation step, and a dehydration step.

Preferably, a compound of Formula III and an equimolar quantity of a compound of Formula II are stirred together in a suitable organic solvent in the presence of at least a two-fold molar quantity of a suitable organic amine and at least a slight excess (and preferably a 1.3-fold to two-fold molar quantity) of a suitable transition metal Lewis acid.

The term "transition metal Lewis acid" refers to chemical compounds comprised of a central transition metal atom and appropriate ligands, such that the central metal atom can form chemical complexes by interaction with electron-rich atoms of other compounds. Preferred transition metals include titanium and zirconium. The term "ligand" refers to an electronegative atom or molecule that can chemically bind to a transition metal atom. Appropriate ligands for the process of this invention include halides, preferably chloride; organic amines; and the like. Suitable transition metal Lewis acids for the process of this invention are transition metal Lewis acids that interact with a compound of Formula III in such a way as to promote condensation at the $CH_3CO$- methyl group. Examples of suitable transition metal Lewis acids are titanium tetrahalides and zirconium tetrahalides. A preferred transition metal Lewis acid is titanium tetrachloride. For synthetic methods using titanium tetrachloride, see (1) B. Weidmann and D. Seebach, *Angew. Chem. Int. Ed. Engl.*, 22, 31-45 (1983); (2) M. T. Reetz, "Organotitanium Reagents in Organic Synthesis. A Simple Means to Adjust Reactivity and Selectivity of Carbanions" in *Top. Curr. Chem.*, 106, 1-54 (1982); and (3) T. Mukaiyama, *Angew. Chem. Int. Ed. Engl.*, 16, 817-826 (1977).

Suitable organic solvents are organic liquids in which reactants may be dissolved or suspended but which are otherwise chemically inert. Examples of suitable organic solvents include alkanes and cycloalkanes; ethers and cyclic ethers; aromatic hydrocarbons; halocarbons, such as chloroform, dichloromethane, ethylene dichloride; and the like. Preferred organic solvents include tetrahydrofuran and dichloromethane, preferably tetrahydrofuran.

Suitable organic amines are basic nitrogen-containing organic compounds that are sufficiently basic to prevent the reaction medium from becoming acidic but which do not themselves form significant quantities of byproducts by chemical reaction with other reagents. Suitable organic amines include tertiary amines and hindered secondary amines. Suitable tertiary amines include trialkylamines, such as triethylamine and tributylamine; N-substituted heterocyclic compounds, such as N-methylmorpholine, N-methylpiperidine, and N,N'-dimethylpiperazine; polybasic tertiary amines, such as N,N,N',N'-tetramethylethylenediamine and N,N,N',N'-tetramethylpropylenediamine; and other tertiary amines known in the art. As used herein, the term "hindered secondary amine" refers to a secondary amine bearing sterically bulky substituents. Suitable hindered secondary amines include 2,2,6,6-tetramethylpiperidine and other hindered secondary amines known in the art. Preferred organic amines are tertiary amines, preferably triethylamine, N-methylmorpholine, and N,N,N',N'-tetramethylethylenediamine.

Although titanium tetrachloride is typically added as a solution in carbon tetrachloride, an alternative embodiment employs a preformed complex of N,N,N',N'-tetramethylethylenediamine and titanium tetrachloride, which may be used where titanium tetrachloride is required and which may be used with or without adding excess N,N,N',N'-tetramethylethylenediamine or other suitable organic amine. The preparation of complexes of titanium tetrachloride and diamines are well known in the art, for example, R. Tabacchi, L. Vuitel, and A. Jacot-Guillarmod, *Helv. Chim. Acta*, 53, 1495-1499 (1970).

The order of addition of the individual reagents to the reaction vessel is generally not critical, although the particular order of addition may in some cases alter the yield or purity of compounds of this invention. The preferred order of addition for any particular reaction may depend upon the specific reagents used and the product desired. In a typical reaction sequence, titanium tetrachloride (or other similar transition metal Lewis acid) in carbon tetrachloride is first added to the organic solvent, preferably tetrahydrofuran or dichloromethane; normally, an equimolar to four-fold molar quantity of titanium tetrachloride relative to the quantity of the compound of Formula III is used. Although this addition and the subsequent reaction steps may be performed over a temperature range of about 75° C. down to about −60° C., the titanium tetrachloride is generally added to the solvent at temperatures between about 0° C. and −50° C. An acetoacetate ester, acetoacetamide, or 2,4-alkanedione of Formula III is added, preferably while the temperature of the titanium tetrachloride mixture is maintained between 0° C. and 40° C. The organic amine, typically in a two-fold to eight-fold molar quantity relative to the compound of Formula III, is next added. Finally, an equimolar quantity (relative to the compound of Formula III) of an optionally substituted benzaldehyde of Formula II is added and the reaction allowed to proceed to completion. Compounds of this invention may be isolated by methods known to those skilled in the art. A preferred isolation procedure involves adding water to the reaction mixture and performing solvent-solvent extraction, followed by chromatography. Condensation at the CH₃CO- methyl group rather than at the —CO—CH₂—CO— methylene group is readily determined by one skilled in the art using modern analytical methods. A preferred analytical method is nuclear magnetic spectroscopy (nmr), by which disappearance of the nmr signal attributable to the methyl group (but not the methylene group) indicates condensation only at the methyl group.

Symmetrical bis(phenylalkene)diones of this invention, Formula IV

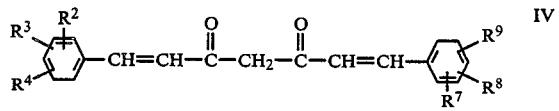

wherein $R^2$, $R^3$, $R^4$, $R^7$, $R^8$, and $R^9$ are defined the same as above for compounds of Formula I, may be formed by the reaction of an excess of an optionally substituted benzaldehyde of Formula II with 2,4-pentanedione (i.e., Formula III wherein $R^1$ is methyl) under conditions similar to those described above.

The compounds of this invention exhibited in vitro inhibition of leukotriene biosynthesis. The leukotriene inhibitory activity of the compounds of this invention illustrated in the examples was tested by the following method.

Inhibition of Leukotriene Biosynthesis

Leukotriene C₄ (LTC₄) and leukotriene D₄ (LTD₄) biosynthesis by cultured rat basophilic leukemia cells (RBL-1 cells) was induced by incubation of the cells with an ionophore. See B. A. Jakschik, S. Falkenheim, and C. W. Parker, "Precursor Role of Arachidonic Acid in Release of Slow Reacting Substance from Rat Basophilic Leukemia Cells," *Proc. Natl. Acad. Sci. U.S.A.*, 74, 4577–4581 (1977). The LTC₄ and LTD₄ biosynthesis was quantitated at LTC₄ equivalents by radioimmunoassay using the Leukotriene C₄ [³H]-RIA Kit available commercially from New England Nuclear, 549 Albany Street, Boston, MA. Compounds were screened initially at 10⁻⁴ M or 10⁻⁵ M and compared with nordihydroguaiaretic acid (the reference standard). A compound inhibiting leukotriene synthesis at any given concentration by at least 30% relative to the reference standard was considered active. An IC₅₀ was determined for each compound exhibiting at least 50% inhibition at the initial screening dose. Table A lists IC₅₀'s for representative compounds of this invention.

TABLE A

| Inhibition of Leukotriene Biosynthesis | |
|---|---|
| Compound | IC₅₀ (μM) |
| Example 1 | 20.0 |
| Example 20 | 27.0 |
| Example 21 | 26.5 |
| Example 23 | 67.0 |
| Example 27 | 27.2 |

With respect to inhibition of leukotriene biosynthesis, the preferred embodiments of this invention include the use of compounds of the following general structure, preferably as the pharmaceutical compositions thereof:

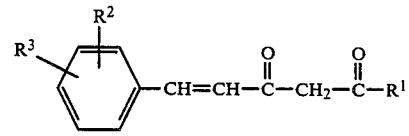

wherein $R^1$ is $C_1$-$C_{10}$ alkyl or $C_1$-$C_6$ alkoxy; and wherein $R^2$ is hydrogen and $R^3$ is hydrogen, $C_1$-$C_{10}$ alkyl, $C_1$-$C_6$ alkoxy, nitro, halogen, hydroxy, phenoxy, or p-chlorophenoxy, or $R^2$ and $R^3$ together are —CH=CH—CH=CH—.

The most preferred embodiments of this invention include the use of compounds of the following general structure, preferably as the pharmaceutical compositions thereof:

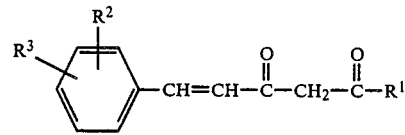

wherein $R^1$ is $C_1$-$C_6$ alkoxy; and wherein $R^2$ is hydrogen and $R^3$ is hydrogen, $C_1$-$C_{10}$ alkyl, $C_1$-$C_6$ alkoxy, halogen, phenoxy, or p-chlorophenoxy, or $R^2$ and $R^3$ together are —CH=CH—CH=CH—.

By virtue of their activity as inhibitors of leukotriene biosynthesis, the compounds of Formula I are useful in treating conditions associated with leukotrienes, such as allergic reactions, particularly asthma; inflammatory conditions; and coronary vasoconstriction. A physician or veterinarian of ordinary skill can readily determine whether a subject exhibits the condition. The preferred utility relates to treatment of allergic reactions. Regardless of the route of administration selected, the compounds of the present invention are formulated into pharmaceutically acceptable dosage forms by conventional methods known to those skilled in the art.

The compounds can be administered in such oral dosage forms as tablets, capsules, pills, powders, granules, elixirs, or syrups. The compounds may also be administered intravascularly, intraperitoneally, subcutaneously, intramuscularly, topically, or transdermally, using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components may be combined with a suitable carrier such as water, saline, aqueous dextrose, and the like.

By whatever route of administration selected, an effective but non-toxic quantity of the compound is employed in treatment. The dosage regimen for preventing or treating leukotriene-associated conditions with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of about 0.1 mg/kg per day up to about 100 mg/kg per day, preferably in the range of about 0.5 to 50 mg/kg per day.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE PREFERRED EMBODIMENTS

EXAMPLE 1 ethyl 3-oxo-5-phenyl-4-pentenoate, Procedure A

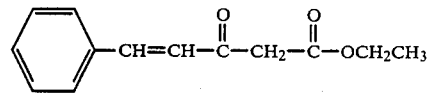

A solution of 6.6 ml (0.06 moles) of titanium tetrachloride in 30 ml of carbon tetrachloride was added dropwise with rapid stirring to 300 ml of cold ($-50°$) tetrahydrofuran. The mixture was allowed to warm to 0° and a solution of 5.85 g (0.045 moles) of ethyl acetoacetate in 50 ml of tetrahydrofuran was added dropwise over about 20 minutes. After the mixture was stirred an additional 30 minutes, a solution of 25.2 ml (0.180 moles) of triethylamine in 50 ml of tetrahydrofuran was added dropwise over 45 minutes. After the mixture was stirred an additional 45 minutes, a solution of 4.8 g (0.045 moles) of benzaldehyde in 50 ml of tetrahydrofuran was added dropwise over 30 minutes. The reaction mixture was allowed to warm to room temperature and then stirred for 24 hours. Water (50 ml) was added and the resultant two-phase mixture was stirred for two hours. After the layers were separated, the aqueous layer was extracted with 50 ml of ethyl acetate. The ethyl acetate extract was combined with the initially separated organic layer, dried over sodium sulfate, filtered, and concentrated in vacuo to 9.8 g of an oil. Chromatography on silica gel gave 7.4 g of the title compound as a solid, m.p. ca. 49°. Structure assignment was supported by nmr and infrared spectra and by elemental analysis.

Analysis. Calcd. for $C_{13}H_{14}O_3$: C, 71.54; H, 6.47. Found: C, 71.78; H, 6.48.

The nmr spectrum (in $CDCl_3$) of the title compound exhibited no signal attributable to $CH_3CO$-protons, but did exhibit signals attributable to $-CO-CH_2-CO-$ methylene protons at $\delta$ 1.44 ppm and to the corresponding enolate $-C(OH)=CH-CO-$vinyl proton at $\delta$ 5.25 ppm.

EXAMPLE 2 ethyl 3-oxo-2-(phenylmethylidene)butanoate

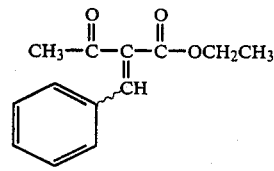

A solution of 5.0 g (0.047 moles) of benzaldehyde, 6.1 g (0.047 moles) of ethyl acetoacetate, and 5 ml of triethylamine in 75 ml. of tetrahydrofuran was stirred at room temperature for 144 hours in the absence of titanium tetrachloride. The reaction mixture was concentrated in vacuo to dryness and the residue chromatographed on silica gel to give both E and Z isomers of the title compound. The products formed by this procedure exhibited nmr signals (in $CDCl_3$) attributable to $CH_3CO-$ but did not exhibit signals characteristic of the title compound of Example 1 (i.e., attributable to —CO—CH$_2$—CO— methylene protons or to the enolate isomer). Structure assignment of the major isomer was also supported by elemental analysis.

Major isomer:
m.p. ca. 58°
nmr (CDCl$_3$): δ (ppm) 2.40 (s, CH$_3$CO); 7.63 (s, —CH=)
Analysis Calcd for C$_{13}$H$_{14}$O$_3$: C, 71.54; H, 6.47. Found: C, 71.52; H, 6.28.

Minor isomer:
nmr (CDCl$_3$): δ (ppm) 2.27 (s, CH$_3$CO); 7.55 (s, —CH=)

EXAMPLE 3 ethyl 3-oxo-5-phenyl-4-pentenoate, Procedure B

The title compound was prepared by the method of Example 1 except that, after the water was added, the mixture was heated at reflux for 20 hours. The material prepared by this procedure was identical to that prepared by the method of Example 1, as indicated by the reverse phase chromatography. The reverse phase chromatographic system employed a 4.6 mm X 25 cm column packed with an octadecyl-bonded silica gel (5 micron particle size) stationary support. Samples containing the reaction products were eluted with a 45:55 (by volume) mixture of acetonitrile and water, and components were detected by ultraviolet absorption at 254 nm.

EXAMPLE 4 ethyl 3-oxo-5-phenyl-4-pentenoate, Procedure C

The title compound was prepared by the method of Example 1 except that the titanium tetrachloride solution in carbon tetrachloride was added to tetrahydrofuran at 0° rather than at −50°. The material prepared by this procedure was identical to that prepared by the method of Example 1, as indicated by the reverse phase chromatographic method described in Example 2.

EXAMPLE 5 ethyl 3-oxo-5-phenyl-4-pentenoate, Procedure D

The title compound was prepared by the method of Example 1 using dichloromethane as solvent instead of tetrahydrofuran. The material prepared by this procedure was identical to that prepared by the method of Example 1, as indicated by the reverse phase chromatographic method described in Example 2.

EXAMPLE 6 ethyl 3-oxo-5-phenyl-4-pentenoate, Procedure E

The title compound was prepared by the method of Example 1 using 2,2,6,6-tetramethylpiperidine as base instead of triethylamine. The material prepared by this procedure was identical to that prepared by the method of Example 1, as indicated by the reverse phase chromatographic method described in Example 2.

EXAMPLE 7 ethyl 3-oxo-5-phenyl-4-pentenoate, Procedure F

The title compound was prepared by the method of Example 1 using N-methylmorpholine as base instead of triethylamine. The material prepared by this procedure was identical to that prepared by the method of Example 1, as indicated by the reverse phase chromatographic method described in Example 2.

EXAMPLE 8 ethyl 3-oxo-5-phenyl-4-pentenoate, Procedure G

The title compound was prepared by the method of Example 7 except that a two-fold molar quantity of titanium tetrachloride relative to ethyl acetoacetate was used. The material prepared by this procedure was identical to that prepared by the method of Example 1, as indicated by the reverse phase chromatographic method described in Example 2.

EXAMPLE 9 ethyl 3-oxo-5-phenyl-4-pentenoate, Procedure H

The title compound was prepared by the method of Example 7 except that a three-fold molar quantity of titanium tetrachloride and a six-fold molar quantity of N-methylmorpholine relative to ethyl acetoacetate were used. The material prepared by this procedure was identical to that prepared by the method of Example 1, as indicated by the reverse phase chromatographic method described in Example 2.

EXAMPLE 10 ethyl 3-oxo-5-phenyl-4-pentenoate, Procedure I

The title compound was prepared by the method of Example 1 using zirconium tetrachloride instead of titanium tetrachloride. The material prepared by this procedure was identical to that prepared by the method of Example 1, as indicated by the reverse phase chromatographic method described in Example 2.

EXAMPLE 11 ethyl 3-oxo-5-phenyl-4-pentenoate, Procedure J

A solution of 0.020 moles of titanium tetrachloride in 5 ml of carbon tetrachloride was added dropwise at room temperature to 50 ml of dichloromethane. The mixture was cooled to 0° and a solution of 0.020 moles of N,N,N',N'-tetramethylethylenediamine in 5 ml of dichloromethane was added dropwise over 15 minutes. After the mixture was stirred an additional hour, a solution of 0.015 moles of ethyl acetoacetate in 10 ml of dichloromethane was added dropwise over 15 minutes. After the mixture was stirred an additional hour, a solution of 0.030 moles of triethylamine in 15 ml of dichloromethane was added over 10 minutes. After thirty minutes, a solution of 0.015 moles of benzaldehyde in 10 ml of dichloromethane was added over 10 minutes. The reaction mixture was stirred for 20 hours. Water (25 ml) was added and the resultant two-phase mixture was stirred for two hours. After the layers were separated, the aqueous layer was extracted with 50 ml of ethyl acetate. The ethyl acetate extract was combined with the initially separated organic layer, dried over sodium sulfate, filtered, and concentrated in vacuo to an oil. Chromatography on silica gel gave the title compound as a solid. The material prepared by this procedure was identical to that prepared by the method of Example 1, as indicated by the reverse phase chromatographic method described in Example 2.

EXAMPLE 12 ethyl 3-oxo-5-phenyl-4-pentenoate, Procedure K

The title compound was prepared by the method of Example 11 using excess N,N,N',N'-tetramethylethylenediamine and no added triethylamine. The material prepared by this procedure was identical to that prepared by the method of Example 1, as indicated by the reverse phase chromatographic method described in Example 2.

EXAMPLE 13 ethyl 3-oxo-5-phenyl-4-pentenoate, Procedure L

The title compound was prepared by the method of Example 1 except that a titanium tetrachloride/N,N,N',N'-tetramethylethylenediamine complex was used instead of titanium tetrachloride alone. The complex was prepared from titanium tetrachloride and N,N,N',N'-tetramethylethylenediamine as described in Example 11 and isolated by filtration.

EXAMPLE 14 ethyl 3-oxo-5-phenyl-4-pentenoate, Procedure M

The title compound was prepared by the method of Example 20 (below) using excess benzaldehyde instead of 3-phenoxybenzaldehyde. The material prepared by this procedure was identical to that prepared by the method of Example 1, as indicated by the reverse phase chromatographic method described in Example 2.

EXAMPLE 15 ethyl 3-oxo-5-phenyl-4-pentenoate, Procedure N

The title compound was prepared by the method of Example 14 except that the reaction was conducted at room temperature instead of 0°. The material prepared by this procedure was identical to that prepared by the method of Example 1, as indicated by the reverse phase chromatographic method described in Example 2.

EXAMPLE 16 ethyl 3-oxo-5-phenyl-4-pentenoate, Procedure O

A solution of 0.020 moles of titanium tetrachloride in 15 ml of carbon tetrachloride was added to a cold (0°) solution of 0.015 moles of ethyl acetoacetate in 75 ml of tetrahydrofuran. After the mixture was stirred for 15 minutes, a solution of 0.060 mole of triethylamine in 15 ml of tetrahydrofuran was added dropwise over five minutes. After the mixture was stirred an additional 15 minutes, a solution of 0.015 moles of benzaldehyde in 15 ml of tetrahydrofuran was added over 10 minutes. The reaction mixture was then stirred for 20 hours, after which the title compound was isolated by the extraction and chromatography methods described in Example 1. The material prepared by this procedure was identical to that prepared by the method of Example 1, as indicated by the reverse phase chromatographic method described in Example 2.

EXAMPLE 17 ethyl 3-oxo-5-phenyl-4-pentenoate, Procedure P

To a cold (5°) solution of 0.015 moles of benzaldehyde and 0.015 moles of ethyl acetoacetate in 60 ml of tetrahydrofuran was added 0.060 mole of triethylamine. After the mixture was stirred for 5 minutes, a solution of 0.020 moles of titanium tetrachloride in 15 ml of carbon tetrachloride was added dropwise over 10 minutes. The reaction mixture was then stirred for 20 hours, after which the title product was isolated by the extraction and chromatography methods described in Example 1. The material prepared by this procedure was identical to that prepared by the method of Example 1, as indicated by the reverse phase chromatographic method described in Example 2.

EXAMPLE 18 ethyl 3-oxo-5-phenyl-4-pentenoate, Procedure Q

A solution of 0.020 moles of titanium tetrachloride in 15 ml of carbon tetrachloride was added over a period of 10 minutes to a cold (5°) solution of 0.015 moles of ethyl acetoacetate and 0.015 moles of benzaldehyde in 60 ml of tetrahydrofuran. After the mixture was stirred for 1.5 hours, a solution of 0.060 mole of triethylamine in 15 ml of tetrahydrofuran was added dropwise. The reaction mixture was then stirred for 20 hours, after which the title compound was isolated by the extraction and chromatography methods described in Example 1. The material prepared by this procedure was identical to that prepared by the method of Example 1, as indicated by the reverse phase chromatographic method described in Example 2.

EXAMPLE 19 ethyl 3-oxo-5-phenyl-4-pentenoate, Procedure R

The title compound was prepared by the method of Example 1 except that the ethyl acetoacetate addition and subsequent steps of the reaction were conducted at 39°. The material prepared by this procedure was identical to that prepared by the method of Example 1, as indicated by the reverse phase chromatographic method described in Example 2.

EXAMPLE 20 ethyl 3-oxo-5-(3-phenoxyphenyl)-4-pentenoate

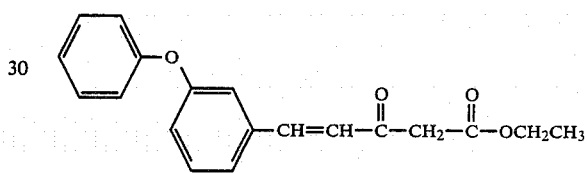

A solution of 0.10 moles of titanium tetrachloride in 25 ml of carbon tetrachloride was added with rapid stirring over 15 minutes to 200 ml of cold (0°) tetrahydrofuran. After the mixture was stirred an additional 15 minutes, a solution of 0.05 moles of 3-phenoxybenzaldehyde in 15 ml of tetrahydrofuran was added over 30 minutes. A solution of 0.05 moles of ethyl acetoacetate in 15 ml of tetrahydrofuran was then added. A solution of 22 ml of N-methylmorpholine in 30 ml of tetrahydrofuran was added dropwise over three hours. The reaction mixture was then stirred for 20 hours, after which time 50 ml of water and 50 ml of diethyl ether were added. After the resultant layers were separated, the aqueous layer was extracted with 50 ml of diethyl ether. The diethyl ether extract was combined with the initially separated organic layer, dried over sodium sulfate, filtered, and concentrated in vacuo to an oil. Chromatography on silica gel gave the title compound as an oil. Structure assignment was supported by nmr and infrared spectra and by elemental analysis.

Analysis. Calcd. for $C_{19}H_{18}O_4$: C, 73.53; H, 5.85. Found: C, 73.72; H, 6.20.

EXAMPLE 21 ethyl 5-[3-(4-chlorophenoxy)phenyl]-3-oxo-4-pentenoate

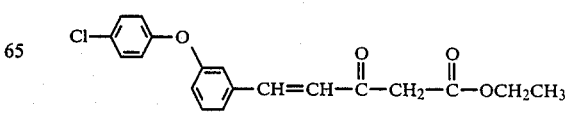

The title compound was prepared by the method of Example 20 using 3-(4-chlorophenoxy)benzaldehyde instead of 3-phenoxybenzaldehyde. Structure assignment was supported by nmr and infrared spectra and by elemental analysis.

Analysis. Calcd. for $C_{19}H_{17}O_4Cl$: C, 66.19; H, 4.97; Cl, 10.28. Found: C, 66.38; H, 5.03; Cl, 10.27.

EXAMPLE 22 ethyl 5-(4-octylphenyl)-3-oxo-4-pentenoate

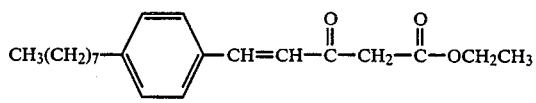

The title compound, m.p. ca. 57°, was prepared by the method of Example 1 using 4-octylbenzaldehyde instead of benzaldehyde. Structure assignment was supported by nmr and infrared spectra and by elemental analysis.

Analysis. Calcd. for $C_{21}H_{30}O_3O$: C, 76.33; H, 9.15. Found: C, 76.22; H, 9.37.

EXAMPLE 23 ethyl 5-(4-methoxyphenyl)-3-oxo-4-pentenoate

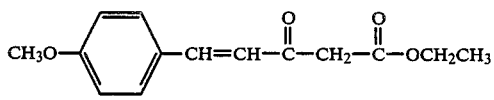

The title compound, m.p. ca. 69°, was prepared by the method of Example 1 using 4-methoxybenzaldehyde instead of benzaldehyde. Structure assignment was supported by nmr and infrared spectra and by elemental analysis.

Analysis. Calcd. for $C_{14}H_{16}O_4$: C, 67.73; H, 6.50. Found: C, 67.67; H, 6.67.

EXAMPLE 24 ethyl 5-(4-nitrophenyl)-3-oxo-4-pentenoate

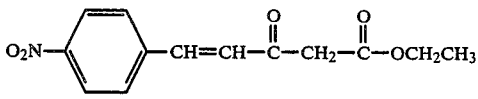

The title compound, m.p. ca. 116°, was prepared by the method of Example 1 using 4-nitrobenzaldehyde instead of benzaldehyde. Structure assignment was supported by nmr and infrared spectra and by elemental analysis.

Analysis. Calcd. for $C_{13}H_{13}NO_5$: C, 59.31; H, 4.98; N, 5.32. Found: C, 59.32; H, 5.01; N, 5.19.

EXAMPLE 25 ethyl 5-(2-nitrophenyl)-3-oxo-4-pentenoate

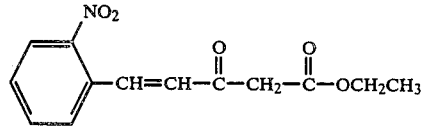

The title compound, m.p. ca. 72°, was prepared by the method of Example 1 using 2-nitrobenzaldehyde instead of benzaldehyde. Structure assignment was supported by nmr and infrared spectra and by elemental analysis.

Analysis. Calcd. for $C_{13}H_{13}NO_5$: C, 59.31; H, 4.98; N, 5.32. Found: C, 59.45; H, 5.17; N, 5.29.

EXAMPLE 26 ethyl 5-(2-hydroxyphenyl)-3-oxo-4-pentenoate

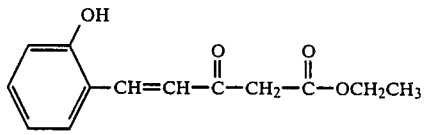

The title compound was prepared as an oil by the method of Example 1 using 2-hydroxybenzaldehyde instead of benzaldehyde. Structure assignment was supported by nmr and infrared spectra.

EXAMPLE 27 ethyl 5-(1-naphthyl)-3-oxo-4-pentenoate

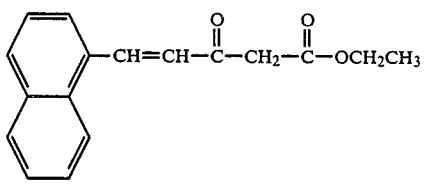

The title compound was prepared as an oil by the method of Example 1 using 1-naphthaldehyde instead of benzaldehyde. Structure assignment was supported by nmr and infrared spectra and by elemental analysis.

Analysis. Calcd. for $C_{17}H_{16}O_3$: C, 76.10; H, 6.01. Found: C, 76.22; H, 6.12.

EXAMPLE 28 methyl 3-oxo-5-phenyl-4-pentenoate

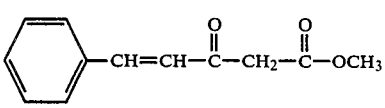

The title compound, m.p. ca. 83°, was prepared by the method of Example 1 using methyl acetoacetate instead of ethyl acetoacetate. Structure assignment was supported by nmr and infrared spectra and by elemental analysis.

Analysis. Calcd. for $C_{12}H_{12}O_3$: C, 70.58; H, 5.92. Found: C, 70.92; H, 6.07.

EXAMPLE 29

N,N-diethyl-3-oxo-5-phenyl-4-pentenamide

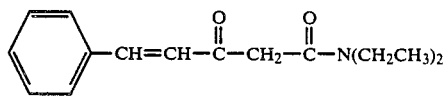

The title compound was prepared by the method of Example 1 using N,N-diethylacetoacetamide instead of ethyl acetoacetate. Structure assignment was supported by nmr and infrared spectra and by elemental analysis.

Analysis. Calcd. for $C_{15}H_{19}NO_2$: C, 73.44; H, 7.81; N, 5.71. Found: C, 73.27; H, 7.86; N, 5.74

EXAMPLE 30

6-phenyl-5-hexene-2,4-dione, Procedure S

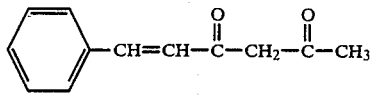

The title compound, m.p. ca. 82°, was prepared by the method of Example 1 using 2,4-pentanedione instead of ethyl acetoacetate. Structure assignment was supported by nmr and infrared spectra and by elemental analysis.

Analysis. Calcd. for $C_{12}H_{12}O_2$: C, 76.57; H, 6.43. Found: C, 76.51; H, 6.36.

EXAMPLE 31

6-phenyl-5-hexene-2,4-dione, Procedure T

The title compound was prepared by the method of Example 6 (that is, using 2,2,6,6-tetramethylpiperidine as base instead of triethylamine) using 2,4-pentanedione instead of ethyl acetoacetate. The material prepared by this procedure was identical to that prepared by the method of Example 30, as indicated by the reverse phase chromatographic method described in Example 2.

EXAMPLE 32

1,7-diphenyl-1,6-heptadiene-3,5-dione

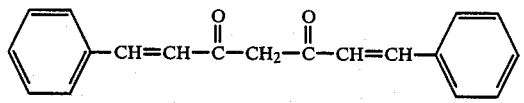

Later chromatographic fractions from the preparation described in Example 30 afforded the title compound, m.p. ca. 138°. Structure assignment was supported by nmr and infrared spectra and by elemental analysis.

Analysis. Calcd. for $C_{19}H_{16}O_2$: C, 82.58; H, 5.84. Found: C, 82.29; H, 5.78.

EXAMPLE 33

1,5-diphenyl-4-pentene-1,3-dione

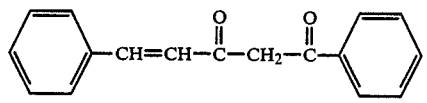

The title compound, m.p. ca. 108°, was prepared by the method of Example 1 using 1-benzoylacetone instead of ethyl acetoacetate. Structure assignment was supported by nmr and infrared spectra and by elemental analysis.

Analysis. Calcd. for $C_{17}H_{14}O_2$: C, 81.58; H, 5.64. Found: C, 81.42; H, 5.59.

What is claimed is:

1. A process for preparing a 5-phenyl-1,3-dioxoalkenyl compound of the formula

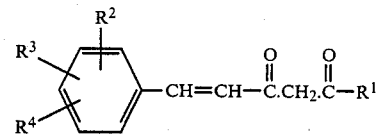

wherein $R^1$ is:
  (a) hydrogen;
  (b) $C_1$–$C_{10}$ alkyl
  (c) $C_1$–$C_6$ alkoxy;
  (d) $NR^5R^6$;
wherein $R^5$ and $R^6$, each being the same or different, are:
  (i) hydrogen; or
  (ii) $C_1$–$C_{10}$ alkyl;
  (e) phenyl or phenyl substituted with 1 to 3 substiuents selected from the group consisting of:
    (i) $C_1$–$C_{10}$ alkyl;
    (ii) $C_1$–$C_6$ alkoxy;
    (iii) nitro, with the proviso that only one such substituent may be nitro; or
    (iv) halogen;
  (f) phenoxy or phenoxy substituted with 1 to 3 substituents selected from the group consisting of:
    (i) $C_1$–$C_{10}$ alkyl;
    (ii) $C_1$–$C_6$ alkoxy;
    (iii) nitro, with the proviso that only one such substituent may be nitro; or
    (iv) halogen;
  (g)

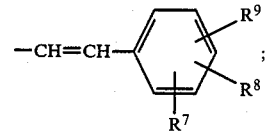

wherein $R^7$, $R^8$, and $R^9$, each being the same or different, are:
  (i) hydrogen;
  (ii) $C_1$–$C_{10}$ alkyl;
  (iii) $C_1$–$C_6$ alkoxy;
  (iv) benzyl;
  (v) phenoxy or phenoxy substituted with 1 to 3 substituents selected from the group consisting of:
    (A) $C_1$–$C_{10}$ alkyl;
    (B) $C_1$–$C_6$ alkoxy; or
    (C) halogen;
  (vi) nitro, with the proviso that only one of $R^7$, $R^8$, and $R^9$ may be nitro;
  (vii) halogen;
  (viii) hydroxyl; or
  (ix) $R^7$ and $R^8$ together are —CH=CH—CH=CH—;
wherein $R^2$, $R^3$, and $R^4$, each being the same or different, are:
  (a) hydrogen;
  (b) $C_1$–$C_{10}$ alkyl;
  (c) $C_1$–$C_6$ alkoxy;
  (d) benzyl;
  (e) phenoxy or phenoxy substituted with 1 to 3 substituents selected from the group consisting of:
    (i) $C_1$–$C_{10}$ alkyl;
    (ii) $C_1$–$C_6$ alkoxy; or (iii) halogen;
(f) nitro, with the proviso that only one of $R^2$, $R^3$, and $R^4$ may be nitro;
(g) halogen;
(h) hydroxyl; or
(i) $R^2$ and $R^3$ together are —CH=CH—CH=CH—;
comprising contacting in an organic solvent at a temperature between −60° C. and 75° C.
(a) an optionally substituted benzaldehyde of the formula

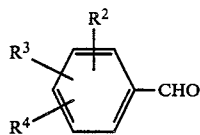

wherein $R^2$, $R^3$, $R^4$ are above defined;
(b) an acetoacetate ester, acetoacetamide, or 2,4-alkanedione of the formula

wherein $R^1$ is:
(a) hydrogen;
(b) $C_1$–$C_{10}$ alkyl;
(c) $C_1$–$C_6$ alkoxy;
(d) $NR^5R^6$;
wherein $R^5$ and $R^6$, each being the same or different, are:
(i) hydrogen; or
(ii) $C_1$–$C_{10}$ alkyl;
(e) phenyl or phenyl substituted with 1 to 3 substituents selected from the group consisting of:
(i) $C_1$–$C_{10}$ alkyl;
(i) $C_1$–$C_6$ alkoxy;
(iii) nitro, with the proviso that only one such substituent may be nitro; or
(iv) halogen;
(f) phenoxy or phenoxy substituted with 1 to 3 substituents selected from the group consisting of:
(i) $C_1$–$C_{10}$ alkyl;
(ii) $C_1$–$C_6$ alkoxy;
(iii) nitro, with the provisio that only one such substituent may be nitro; or
(iv) halogen;
(c) a transition metal Lewis acid; and
(d) a tertiary amine or a hindered secondary amine.

2. A process according to claim 1 wherein the transition metal Lewis acid is at titanium tetrahalide.

3. A process according to claim 1 wherein the transition metal Lewis acid is titanium tetrachloride.

4. A process according to claim 1 wherein the transition metal Lewis acid is a zirconium tetrahalide.

5. A process according to claim 1 wherein the transition metal Lewis acid is zirconium tetrachloride.

6. A process according to claim 1 wherein the tertiary amine is triethylamine, N-methylmorpholine, or N,N,N′,N′-tetramethylethylenediamine.

7. A process according to claim 1 wherein the hindered secondary amine is 2,2,6,6-tetramethylpiperidine.

8. A process according to claim 1 wherein the organic solvent is tetrahydrofuran or dichloromethane.

9. A process according to claim 1 wherein the temperature is between 0° C. and 40°.

10. A process according to claim 1 for preparing a 5-phenyl-1,3-dioxoalkenyl compound of the formula

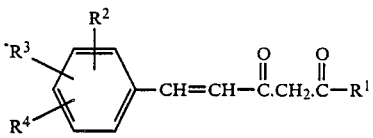

wherein $R^1$ is:
(a) hydrogen;
(b) $C_1$–$C_{10}$ alkyl;
(c) $C_1$–$C_6$ alkoxy;
(d) $NR^5R^6$;
wherein $R^5$ and $R^6$, each being the same or different, are:
(i) hydrogen; or
(ii) $C_1$–$C_{10}$ alkyl;
(e) phenyl or phenyl substituted with 1 to 3 substituents selected from the group consisting of:
(i) $C_1$–$C_{10}$ alkyl;
(ii) $C_1$–$C_6$ alkoxy;
(iii) nitro, with the proviso that only one such substituent may be nitro; or
(iv) halogen;
(f) phenoxy or phenoxy substituted with 1 to 3 substitutents selected from the group consisting of:
(i) $C_1$–$C_{10}$ alkyl;
(ii) $C_1$–$C_6$ alkoxy;
(iii) nitro, with the proviso that only one such substitutent may be nitro; or
(iv) halogen;
wherein $R^2$, $R^3$, and $R^4$, each being the same or different, are:
(a) hydrogen;
(b) $C_1$–$C_{10}$ alkyl;
(c) $C_1$–$C_6$ alkoxy;
(d) benzyl;
(e) phenoxy or phenoxy substituted with 1 to 3 substituents selected from the group consisting of:
(i) $C_1$–$C_{10}$ alkyl;
(ii) $C_1$–$C_6$ alkoxy; or
(iii) halogen;
(f) nitro, with the proviso that only one of $R^2$, $R^3$, and $R^4$ may be nitro;
(g) halogen;
(h) hydroxyl; or
(i) $R^2$ and $R^3$ together are —CH=CH—CH=CH—;
comprising contacting in an organic solvent at a temperature between −60° C. and 75° C.
(a) 1 part by moles of an optionally substituted benzaldehyde;
(b) 1 part by moles of acetoacetate ester, acetoacetamide, or 2,4-alkanedione;
(c) 1 to 4 parts by moles of a transition metal Lewis acid; and
(d) 2 to 8 parts by moles of a tertiary amine or a hindered secondary amine.

11. A process according to claim 10 for preparing a 5-phenyl-1,3-dioxoalkenyl compound comprising contacting in tetrahydrofuran at a temperature between 0° C. and 40° C.
(a) 1 part by moles of an optionally substituted benzaldehyde;
(b) 1 part by moles of an acetoacetate ester, acetoacetamide, or 2,4-alkanedione;
(c) 1 to 3 parts by moles of titanium tetrachloride; and (d) 2 to 4 parts by moles of triethylamine.

12. A process according to claim 11 for preparing a 5-phenyl-1,3-dioxoalkenoate ester of the formula

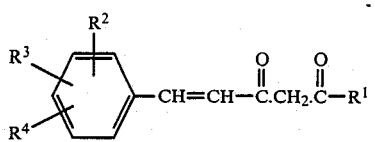

wherein $R^1$ is:
(a) $C_1$-$C_6$ alkoxy; or
(b) phenoxy or phenoxy substituted with 1 to 3 substituents selected from the group consisting of:
(i) $C_1$-$C_{10}$ alkyl
(ii) $C_1$-$C_6$ alkoxy;
(iii) nitro, with the proviso that only one such substituent may be nitro; or
(iv) halogen;
wherein $R^2$, $R^3$, and $R^4$, each being the same or different, are:
(a) hydrogen;
(b) $C_1$-$C_{10}$ alkyl;
(c) $C_1$-$C_6$ alkoxy;
(d) benzyl;
(e) phenoxy or phenoxy substituted with 1 to 3 substituents selected from the group consisting of:
(i) $C_1$-$C_{10}$ alkyl;
(ii) $C_1$-$C_6$ alkoxy; or
(iii) halogen;
(f) nitro, with the proviso that only one of $R^2$, $R^3$, and $R^4$ may be nitro;
(g) halogen;
(h) hydroxyl; or
(i) $R^2$ and $R^3$ together are —CH=CH—CH=CH—;
comprising contacting in tetrahydrofuran at a temperature between 0° C. and 40° C.
(a) 1 part by moles of an optionally substituted benzaldehyde;
(b) 1 part by moles of an acetoacetate ester of the formula

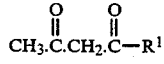

wherein $R^1$ is:
(a) $C_1$-$C_6$ alkoxy; or
(b) phenoxy or phenoxy substituted with 1 to 3 substituents selected from the group consisting of:
(i) $C_1$-$C_{10}$ alkyl;
(ii) $C_1$-$C_6$ alkoxy;
(iii) nitro, with the proviso that only one such substituent may be nitro; or
(iv) halogen;
(c) 1 to 3 parts by moles of titanium tetrachloride; and
(d) 2 to 4 parts by moles of triethylamine.

13. A process according to claim 11 for preparing a 5-phenyl-1,3-dioxoalkenamide of the formula

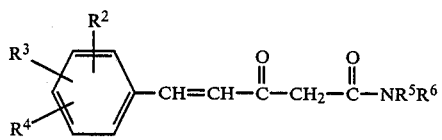

wherein $R^5$ and $R^6$, each being the same or different, are:
(a) hydrogen; or
(b) $C_1$-$C_{10}$ alkyl; comprising contacting in tetrahydrofuran at a temperature between 0° C. and 40° C.
(a) 1 part by moles of an optionally substituted benzaldehyde;
(b) 1 part by moles of an acetoacetamide of the formula

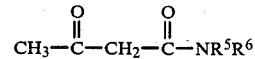

wherein $R^5$ and $R^6$, each being the same or different, are:
(a) hydrogen; or
(b) $C_1$-$C_{10}$ alkyl;
(c) 1 to 3 parts by moles of titanium tetrachloride; and
(d) 2 to 4 parts by moles of triethylamine.

14. A process according to claim 11 for preparing a 5-phenyl-1,3-dioxoalkenyl compound of the formula

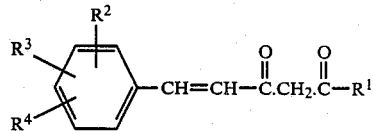

wherein $R^1$ is:
(a) hydrogen;
(b) $C_1$-$C_{10}$ alkyl;
(c) phenyl or phenyl substituted with 1 to 3 substituents selected from the group consisting of:
(i) $C_1$-$C_{10}$ alkyl;
(ii) $C_1$-$C_6$ alkoxy;
(iii) nitro, with the proviso that only one such substituent may be nitro; or
(iv) halogen;
wherein $R^2$, $R^3$, and $R^4$, each being the same or different, are:
(a) hydrogen;
(b) $C_1$-$C_{10}$ alkyl;
(c) $C_1$-$C_6$ alkoxy;
(d) benzyl;
(e) phenoxy or phenoxy substituted with 1 to 3 substituents selected from the group consisting of:
(i) $C_1$-$C_{10}$ alkyl;
(ii) $C_1$-$C_6$ alkoxy; or
(iii) halogen;
(f) nitro, with the proviso that only one of $R^2$, $R^3$, and $R^4$ may be nitro;
(g) halogen;
(h) hydroxyl; or
(i) $R^2$ and $R^3$ together are —CH=CH—CH=CH—;
comprising contacting in tetrahydrofuran at a temperature between 0° C. and 40° C.
(a) 1 part by moles of an optionally substituted benzaldehyde;
(b) 1 part by moles of a 2,4-alkanedione of the formula

wherein $R^1$ is:

(a) hydrogen;
(b) $C_1$-$C_{10}$ alkyl;
(c) phenyl or phenyl substituted with 1 to 3 substituents selected from the group consisting of:
  (i) $C_1$-$C_{10}$ alkyl;
  (ii) $C_1$-$C_6$ alkoxy;
  (iii) nitro, with the provisio that only one such substituent may be nitro; or
  (iv) halogen;
(c) 1 to 3 parts by moles of titanium tetrachloride; and
(d) 2 to 4 parts by moles of triethylamine.

15. A process according to claim 1 for preparing a 1,7-diphenyl-1,6-heptadiene-3,5-dione compound of the formula

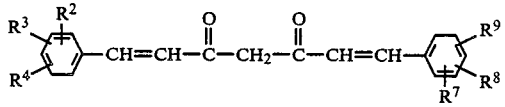

wherein $R^2$, $R^3$, and $R^4$, each being the same or different, are:
(a) hydrogen;
(b) $C_1$-$C_{10}$ alkyl;
(c) $C_1$-$C_6$ alkoxy;
(d) benzyl;
(e) phenoxy or phenoxy substituted with 1 to 3 substituents selected from the group consisting of:
  (i) $C_1$-$C_{10}$ alkyl;
  (ii) $C_1$-$C_6$ alkoxy; or
  (iii) halogen;
(f) nitro, with the provisio that only one of $R^2$, $R^3$, and $R^4$ may be nitro;
(g) halogen;
(h) hydroxyl; or
(i) $R^2$ and $R^3$ together are —CH=CH—CH=CH—;
wherein $R^7$, $R^8$, and $R^9$, each being the same or different, are:
(a) hydrogen;
(b) $C_1$-$C_{10}$ alkyl;
(c) $C_1$-$C_6$ alkoxy;
(d) benzyl;
(e) phenoxy or phenoxy substituted with 1 to 3 substitutents selected from the group consisting of:
  (i) $C_1$-$C_{10}$ alkyl;
  (ii) $C_1$-$C_6$ alkoxy; or
  (iii) halogen;
(f) nitro, with the proviso that only one of $R^7$, $R^8$, and $R^9$ may be nitro;
(g) halogen;
(h) hydroxyl; or
(i) $R^7$ and $R^8$ together are —CH=CH—CH=CH—;
comprising contacting in tetrahydrofuran at a temperature between $-60°$ C. and 75° C.
(a) 2 to 5 parts by moles of an optionally substituted benzaldehyde;
(b) 1 part by moles of 2,4-pentanedione;
(c) 1 to 4 parts by moles of a transition metal Lewis acid; and
(d) 2 to 8 parts by moles of a tertiary amine or a hindered secondary amine.

16. A process according to claim 15 for preparing a 1,7-diphenyl-1,6-heptadiene-3,5-dione compound comprising contacting in tetrahydrofuran at a temperature between 0° C. and 40° C.
(a) 2 to 5 parts by moles of an optionally substituted benzaldehyde;
(b) 1 part by moles of 2,4-pentanedione;
(c) 1 to 3 parts by moles of titanium tetrachloride; and
(d) 2 to 4 parts by moles of triethylamine.

* * * * *

UNITED STATES PATENT AND TRADEMARK OFFICE
CERTIFICATE OF CORRECTION

PATENT NO. : 4,761,503

DATED : August 2, 1988

INVENTOR(S) : Partis, et al.

It is certified that error appears in the above-identified patent and that said Letters Patent is hereby corrected as shown below:

Column 3, the first structure, that portion of the structure reading $-\overset{O}{\overset{\|}{C}}.CH_2.\overset{O}{\overset{\|}{C}}-R^1$ should read $-\overset{O}{\overset{\|}{C}}-CH_2-\overset{O}{\overset{\|}{C}}-R^1$ Column 18, the first structure, that portion of the structure reading $-\overset{O}{\overset{\|}{C}}.CH_2.\overset{O}{\overset{\|}{C}}-R^1$ should read $-\overset{O}{\overset{\|}{C}}-CH_2-\overset{O}{\overset{\|}{C}}-R^1$ Column 19, lines 23-25, the formula reading $CH_3.\overset{O}{\overset{\|}{C}}.CH_2.\overset{O}{\overset{\|}{C}}-R^1$ should read $CH_3-\overset{O}{\overset{\|}{C}}-CH_2-\overset{O}{\overset{\|}{C}}-R^1$ Column 20, the first structure, that portion of the structure reading $-\overset{O}{\overset{\|}{C}}.CH_2.\overset{O}{\overset{\|}{C}}-R^1$ should read $-\overset{O}{\overset{\|}{C}}-CH_2-\overset{O}{\overset{\|}{C}}-R^1$ Column 21, the first structure, that portion of the structure reading $-\overset{O}{\overset{\|}{C}}.CH_2.\overset{O}{\overset{\|}{C}}-R^1$ should read $-\overset{O}{\overset{\|}{C}}-CH_2-\overset{O}{\overset{\|}{C}}-R^1$ Column 21, lines 45-47, the formula reading $CH_3.\overset{O}{\overset{\|}{C}}.CH_2.\overset{O}{\overset{\|}{C}}-R^1$ should read $CH_3-\overset{O}{\overset{\|}{C}}-CH_2-\overset{O}{\overset{\|}{C}}-R^1$

UNITED STATES PATENT AND TRADEMARK OFFICE
CERTIFICATE OF CORRECTION

PATENT NO. : 4,761,503
DATED : August 2, 1988
INVENTOR(S) : Partis, et al.

It is certified that error appears in the above-identified patent and that said Letters Patent is hereby corrected as shown below:

Column 22, the second structure, that portion of the structure reading
$$-\overset{O}{\underset{\|}{C}}.CH_2.\overset{O}{\underset{\|}{C}}-R^1 \quad \text{should read} \quad -\overset{O}{\underset{\|}{C}}-CH_2-\overset{O}{\underset{\|}{C}}-R^1$$

Column 22, lines 64-66, the formula reading
$$CH_3.\overset{O}{\underset{\|}{C}}.CH_2.\overset{O}{\underset{\|}{C}}-R^1 \quad \text{should read} \quad CH_3-\overset{O}{\underset{\|}{C}}-CH_2-\overset{O}{\underset{\|}{C}}-R^1$$

Signed and Sealed this

Third Day of April, 1990

Attest:

HARRY F. MANBECK, JR.

*Attesting Officer*  *Commissioner of Patents and Trademarks*